United States Patent [19]
Kleemiss et al.

[11] Patent Number: 6,143,920
[45] Date of Patent: Nov. 7, 2000

[54] PROCESS FOR THE PREPARATION OF METHOXYACETIC ACID ESTERS

[75] Inventors: Wolfgang Kleemiss, Haltern; Klaus-Dieter Steffen, Hennef; Marcel Feld, Cologne, all of Germany

[73] Assignee: Huels Aktiengesellschaft, Marl, Germany

[21] Appl. No.: 09/179,189

[22] Filed: Oct. 27, 1998

[30] Foreign Application Priority Data

Dec. 15, 1997 [DE] Germany ............................ 197 55 599

[51] Int. Cl.[7] .............................. C07C 69/66; C07C 67/02
[52] U.S. Cl. ............................................................ 560/187
[58] Field of Search ............................................. 560/187

[56] References Cited

U.S. PATENT DOCUMENTS 2,452,350  10/1948  Bitler et al. .
4,898,969   2/1990  Jones et al. .
6,005,139  12/1999  Chen et al. .............................. 560/187

OTHER PUBLICATIONS

Otera, J. "Transesterification" Chem. Rev. vol. 93 pp. 1449–1470. See entire article, 1993.

Primary Examiner—Howard C. Lee
Assistant Examiner—Leigh C. Maier
Attorney, Agent, or Firm—Oblon, Spivak, McClelland, Maier & Neustadt, P.C.

[57] ABSTRACT

The invention relates to a process for the preparation of methoxyacetic acid esters in which a chloroacetic acid ester is reacted with an alkali metal methoxide to give the methoxyacetic acid ester.

17 Claims, No Drawings

PROCESS FOR THE PREPARATION OF METHOXYACETIC ACID ESTERS

BACKGROUND OF THE INVENTION

1. Field of the Invention

The invention relates to a process for the preparation of methoxyacetic acid esters by reaction of chloroacetic acid esters with an alkali metal methoxide.

2. Discussion of the Background

Methoxyacetic acid esters are valuable intermediates which can be used, for example, for the kinetic resolution of chiral amines (F. Balkenhohl, K. Ditrich, B. Hauer, W. Ladner, J. prakt. Chem. 339 (1997), 381–384; DE-A 195 23 151). In this case, high demands are placed on the purity of the methoxyacetic acid ester. since the lipase used for the resolution is easily inhibited by impurities. A content of chloroacetic acid ester and of water is particularly critical here.

Methoxyacetic acid esters can be prepared in principle by esterification of methoxyacetic acid (Paloma, Jakkola, Chem. Ber. 67 (1967), 954; G. G. Smith et al., J. Org. Chem. 42 (1977), 44–47; Kumar, K. Amal. Chattopadhay, K. Tapas, Tetrahedron Lett. 28 (1987), 3713–3714). The yields achieved in this case of up to 60% are, however, not satisfactory.

Moreover, methoxyacetic acid is only accessible with difficulty. It can be prepared, for example, by nitric acid or electrochemical oxidation of ethylene glycol monomethyl ether (DE-A 32 09 622; EP 0 048 396; DE-A 36 20 013). In the electrochemical oxidation, the sodium salt results primarily, which then has to be converted into the free methoxyacetic acid using another acid. In this case the sodium salt of this other acid is formed as an unavoidable product, which has to be disposed of. In the nitric acid oxidation, a 2.5-fold stoichiometric excess of nitric acid has to be used. Finally, ethylene glycol monomethyl ether can also be oxidized to methoxyacetic acid by catalytic oxidation with atmospheric oxygen (DE 93 61 23), which is obtained here, however, as a highly dilute aqueous solution and has to be distilled with expenditure of energy to give the anhydrous product. All oxidation processes starting from ethylene glycol monomethyl ether additionally have the disadvantage that in the reaction product, beside reaction by-products, starting substance is also still present. Ethylene glycol monomethyl ether however, is suspected of being embryo toxic, so when working with methoxyacetic acid or the corresponding esters contaminated in this way particular caution is advisable.

Methyl methoxyacetate is also accessible by carbonylation of methanol (U.S. Pat. No. 4,482,735) or of formaldehyde dimethyl acetal (EP 0 071 920). The selectivities and thus the yields of the respective carbonylation reactions, however, are low, so the processes are completely unsuitable for economical production of the methoxyacetic acid esters.

A further, readily accessible starting material for the preparation of methoxyacetic acid esters is chloroacetic acid. It is possible to convert its alkali metal salts or the ammonium salt into the alkali metal or ammonium salt of methoxyacetic acid using alkali metal methoxide (DE A 29 48 200). This is converted by protonation into methoxyacetic acid, which then has to be esterified, as described before. This process is already uneconomical because of the unsatisfactory yields of the esterification step and is moreover associated with a large yield of salt.

SUMMARY OF THE INVENTION

An essential object of the invention is to make available an economical process starting from readily accessible, inexpensive starting materials, which in a simple manner affords methoxyacetic acid esters in good yields and in high purity.

It has now been found that this object is achieved by a process for the preparation of methoxyacetic acid esters, in which a chloroacetic acid ester is reacted with an alkali metal methoxide to give the methoxyacetic acid ester. This can be transesterified, if desired after its isolation from the reaction mixture or directly in the reaction mixture. This transesterification takes place particularly simply if the methoxyacetic acid ester is transesterified with a higher alcohol. In this way, for example, methyl methoxyacetate can be converted into methoxyacetic acid esters of any desired higher alcohols by reaction with a higher alcohol and removal of methanol by distillation.

DETAILED DESCRIPTION OF THE PREFERRED EMBODIMENTS

Good yields are also achieved by the process according to the invention using excess alkali metal alcoholates which, depending on the ester, can be up to 90%. This is surprising, because it is known that methyl methoxyacetate affords a condensation product in the presence of alkali metal methoxide (H. Adkins, R. M. Elofson, A. G. Rossow, C. C. Robinson: J. Am. Soc. 71, 3622 [1949]).

It is furthermore surprising that methoxyacetic acid ester can be transesterified directly in the reaction mixture of the reaction of chloroacetic acid ester with excess alkali metal methoxide, in which alkali metal methoxide is still present in addition to the alkali metal chloride which is formed in the reaction in stoichiometric amounts, with addition of a high alcohol and with removal of the lower alcohol by distillation directly to give the methoxyacetic acid ester of the higher alcohol and this, if appropriate after prior removal of the alkali metal chloride, can be obtained in high yields by distillation. Customarily, the transesterification catalysts in fact used are Lewis acids, such as alkoxytitanates (D. Seebach et al., Synthesis 1982, p. 138), while the use of the strongly basic alkali metal alcoholates for this purpose is extremely uncustomary.

The low chlorine content of the methoxyacetic acid esters prepared directly and of the higher methoxyacetic acid esters prepared by transesterification therefrom, which is only 5 to 10 ppm, is furthermore surprising. The esters are therefore also suitable and particularly suitable for the mentioned kinetic enzymatic resolution of chiral amines.

Preferred chloroacetic acid esters are those which are derived from alkanols having 1 to 6 carbon atoms or alkoxyalkanols having 3 to 6 carbon atoms. Examples which may be mentioned are the chloroacetic acid esters of methanol, ethanol, 1- or 2-propanol, 1- or 2-butanol, 2-methyl-1-propanol, 1-hexanol and 3-oxa-1-pentanol (or ethyl glycol). The methyl ester and the ethyl ester are particularly preferred.

Any alkali metal methoxide may be used in the present process (e.g. MeOLi, MeONa, MeOK, MeORb, MeOCs, etc.). Apart from potassium methoxide, the preferred alkali metal methoxide is the inexpensive sodium methoxide. The alkali metal methoxide is in general used in an amount from 1 to 2, advantageously from 1 to 1.5 and in particular from 1 to 1.2, mol per mole of chloroacetic acid ester.

The process according to the invention may be expediently carried out at a temperature from 20 to 100° C., preferably from 30 to 100° C., advantageously from 60 to 80° C. The reaction mixture can be worked up by distillation, if appropriate after prior neutralization of the excess alkali metal methoxide, e.g. by means of a mineral acid, such as sulfuric acid.

The methoxyacetic acid ester can be reacted (e.g. transesterified), after its removal by distillation, to give the methoxyacetic acid ester of the higher alcohol or, as mentioned, surprisingly in the reaction mixture by transesterification with a higher alcohol with removal of the lower alcohol by distillation. Suitable higher alcohols are preferably alkanols having 2 to 10 carbon atoms and alkoxyalkanols having 4 to 10 carbon atoms. Specific mention may be made, for example, of 2-ethylhexanol, n-octanol, the nonanols and the decanols, in each case per se or as isomer mixtures; and also 2-ethoxyethanol and 2-n-butoxyethanol. The transesterification is expediently carried out at temperatures from 60 to 250° C., preferably from 80 to 250° C., such that the lower alcohol is distilled off.

Suitable catalysts for the transesterification apart from the alkali metal methoxides mentioned, inter alla, are alkali metal alcoholates of alcohols having 1 to 8 carbon atoms and also Lewis acid catalysts, such as alkoxytitanates or -stannates, iron(III) chloride or tin(II) chloride, or Broenstedt acids, such as 4-toluylsulfonic acid.

Both the preparation of the methoxyacetic acid esters from chloroacetic acid esters and optionally the transesterification can be carried out under ambient pressure, elevated pressure or reduced pressure. Advantageously, the reaction is carried out at a pressure from 0.8 to 3 bar, advantageously from 0.9 to 1.5 bar. It is expedient in the transesterification to correlate pressure and temperature such that the lower alcohol distills off.

For workup of the reaction mixtures, the resulting alkali metal chloride can initially be removed, e.g. by filtration or by suction filtration of the liquid phase from the alkali metal chloride, and the methoxyacetic acid ester obtained by fractionation of the liquid phase, any excess alkali metal alcoholates remaining in the distillation residues. Alternatively, the volatile components can be distilled off from the reaction mixture without fractionation, the alkali metal chloride and also any excess alkali metal alcoholate remaining as a residue, and the methoxyacetic acid ester obtained by fractionation of the distillate.

Having generally described this invention, a further understanding can be obtained by reference to certain specific examples which are provided herein for purposes of illustration only and are not intended to be limiting unless otherwise specified. The following examples are intended to illustrate the invention further, but not to restrict its scope as is defined in the patent claims.

EXAMPLES

Example 1

Isopropyl Methoxyacetate 434.1 g (4.0 mol) of methyl chloroacetate are initially introduced and stirred at 25° C. 756.3 g (4.2 mol) of 30% strength sodium methoxide solution are added dropwise in the course of 2.5 h such that a reaction temperature of 65° C. is not exceeded. After the addition, stirring is continued at reflux temperature for a further 3 h. 436.0 g of methanol are then removed from the reaction mixture by distillation. 480.8 g (8 mol) of isopropanol are added to the residue and the mixture is heated under reflux. In the course of this, methanol is removed via a 0.5 m long Multifil column at a reflux ratio of approximately 1:1 (244.4 g of distillate). After 6.5 h, the conversion of the methyl methoxyacetate to the isopropyl methoxyacetate is >98%. After cooling, the reaction mixture is concentrated to dryness on a rotary evaporator at a maximum bath temperature of 120° C. and a pressure of <15 mbar. A residue of 274.3 g and a distillate of 668.0 g are obtained. The distillate is fractionated through a 0.5 m long Multifil column. Isopropyl methoxyacetate is obtained as the main fraction (390.6 g, yield 74%) with a purity of >99%, a chlorine content of 10 ppm and a water content of <0.05%.

Example 2

Isopropyl Methoxyacetate 434.1 g (4.0 mol) of methyl chloroacetate are initially introduced and stirred at 25° C. 756.3 g (4.2 mol) of 30% strength sodium methoxide solution are added dropwise in the course of 2.5 h such that a reaction temperature of 65° C. is not exceeded. After the addition, stirring is continued at reflux temperature for a further 3 h. 407.5 g of methanol are then separated from the reaction mixture by distillation. 480.8 g (8 mol) of isopropanol are added to the residue and the mixture is heated under reflux. In the course of this, methanol is removed through a 0.5 m long Multifil column at a reflux ratio of approximately 1:1 (291.9 g of distillate). After 6.5 h, the conversion of the methyl methoxyacetate to the isopropyl methoxyacetate is >98%. After cooling, the reaction mixture is filtered off with suction and the residue is washed with 450 g of isopropanol. A residue of 412.1 g and a liquid phase (filtrate and wash liquid) of 969.9 g are obtained. The liquid phase is fractionated through a 0.5 m long Multifil column. Isopropyl methoxyacetate (405.0 g, yield 77%) with an organic purity of >99%, a chlorine content of 10 ppm and a water content of <0.05% is obtained as the main fraction.

Example 3 n-Butyl Methoxyacetate 542.5 g (5.0 mol) of methyl chloroacetate are initially introduced and stirred at 25° C. 945.4 g (5.25 mol) of 30% strength sodium methoxide solution are added dropwise in the course of 2.5 h such that a reaction temperature of 65° C. is not exceeded. After the addition, stirring is continued at reflux temperature for a further 3 h. 518.8 g of methanol are then removed from the reaction mixture by distillation. 741.2 g (10 mol) of n-butanol are added to the residue and the mixture is heated under reflux. In the course of this, methanol is removed through a 0.5 m long Multifil column at a reflux ratio of approximately 1:1 (398.7 g of distillate). After 6.5 h, the conversion of the methyl methoxyacetate to the n-butyl methoxyacetate is >98%. After cooling, the reaction mixture is filtered off with suction and the residue is washed with 277 g of n-butanol. The liquid phase (filtrate and wash liquid) of 1,132.9 g is fractionated through a 0.5 m long Multifil column. n-Butyl methoxyacetate (548.1 g, yield 75%) is obtained as the main fraction with a purity >99%, a chlorine content of 10 ppm and a water content of <0.05%.

Example 4 n-Octyl Methoxyacetate 537.2 g (4.95 mol) of methyl chloroacetate are initially introduced and stirred at 25° C. 936.4 g (5.2 mol) of 30% strength sodium methoxide solution are added dropwise in the course of 2.5 h such that a reaction temperature of 65° is not exceeded. After the addition, stirring is continued at reflux temperature for a further 3 h. 511.9 g of methanol are then removed from the reaction mixture by distillation. 1,289.3 g (9.9 mol) of n-octanol are added to the residue and the mixture is heated under reflux. In the course of this, methanol is removed through a 0.5 m long Multifil column at a reflux ratio of approximately 1:1 (303.5 g of distillate), the bottom temperature rising to 210° C. during the removal. After 6.5 h, the conversion of the methyl methoxyacetate to the n-octyl methoxyacetate is >98%. The reaction mixture is fractionated through a 0.5 m long Multifil column. Initially, n-octanol and methyl methoxyacetate are distilled off n-Octyl methoxyacetate (740.0 g, yield 74%) is then obtained as a main fraction with a purity >99%, a chlorine content of 10 ppm and a water content of <0.05%.

Obviously, numerous modifications and variations of the present invention are possible in light of the above teachings. It is therefore to be understood that within the scope of the appended claims, the invention may be practiced otherwise than as specifically described herein.

This application is based on German patent application 197 55 599.3 filed with the German Patent Office on Dec. 15, 1997 the entire contents of which are hereby incorporated by reference.

What is claimed is:

1. A process for the preparation of a methoxyacetic acid ester, comprising reacting a chloroacetic acid ester with an alkali metal methoxide to give a methoxyacetic acid ester;

transesterifying said first methoxyacetic acid ester with a higher alcohol in the presence of an excess of alkali metal alkoxide catalyst to give a second methoxyacetic acid ester of said higher alcohol; wherein said methoxyacetic acid ester is transesterified without isolation.

2. The process of claim 1, wherein said chloroacetic acid ester is an ester of a $C_{1-6}$ alkanol or a $C_{3-6}$ alkoxy alcohol.

3. The process of claim 1, wherein said alkali metal methoxide is selected from the group consisting of potassium methoxide, sodium methoxide and a mixture thereof, in an amount of from 1 to 2 equivalents per equivalent of chloroacetic acid ester.

4. The process of claim 3, wherein an amount of said alkali metal methoxide is 1 to 1.5 equivalents.

5. The process of claim 3, wherein an amount of said alkali metal methoxide is 1 to 1.2 equivalents.

6. The process of claim 1, wherein said reaction takes place at a temperature of 20 to 10° C.

7. The process of claim 1, wherein said reaction takes place at a temperature of 60 to 80° C.

8. The process of claim 1, wherein said higher alcohol is a $C_{2-10}$ alkanol or a $C_{4-10}$ alkoxyalkanol.

9. The process of claim 1, wherein reaction of said methoxyacetic acid ester is carried out at a temperature from 80 to 250° C.

10. The process of claim 1, wherein transesterification is conducted in the presence of excess alkali metal methoxide.

11. The process of claim 1, wherein said reaction is carried out at a pressure from 0.8 to 3 bar.

12. The process of claim 1, wherein said reaction is carried out at a pressure from 0.5 to 1.5 bar.

13. The process of claim 1, wherein transesterification is carried out at a pressure from 0.8 to 3 bar.

14. The process of claim 1, wherein transesterification is carried out at a pressure from 0.5 to 1.5 bar.

15. The process of claim 1, further comprising removing an alkali metal chloride from said reaction mixture and isolating said methoxyacetic acid ester by fractionation of a liquid phase, any excess alkali metal alcoholate remaining in the residue.

16. The process of claim 1, wherein volatile components are distilled off from the reaction mixture without fractionation, an alkali metal chloride and also any excess alkali metal alcoholate remaining as a residue, and said methoxyacetic acid ester of said higher alcohol is obtained by fractional of the distillate.

17. The process of claim 1, wherein said chloroacetic acid ester is the chloroacetic acid ester an alcohol selected from the group consisting of methanol, ethanol, 1-propanol, 2-propanol, 1-butanol, 2-butanol, 2-methyl-1-propanol, 1-hexanol, 3-oxa-1-pentanol, ethyl glycol and a mixture thereof.

* * * * *